United States Patent [19]

Schulz

[11] 4,150,040
[45] Apr. 17, 1979

[54] AROMATIC ANHYDRIDES

[75] Inventor: J. Gustav Schulz, Pittsburgh, Pa.

[73] Assignee: Gulf Research & Development Company, Pittsburgh, Pa.

[21] Appl. No.: 696,742

[22] Filed: Jun. 16, 1976

[51] Int. Cl.² .......................................... C07D 307/89
[52] U.S. Cl. ............................ 260/346.3; 260/346.4; 562/410
[58] Field of Search ............ 260/346.3, 346.4, 515 H, 260/515 P

[56] References Cited

U.S. PATENT DOCUMENTS 3,153,666  10/1964  Higuchi et al. ..................... 260/515
3,466,301  9/1969   McCracken et al. ............. 260/346.4

OTHER PUBLICATIONS

Higuchi et al., Ch. Abst., vol. 50 (1956), 10044d.
Polansky et al., Ind. and Eng. Chem., vol. 39, No. 7, (1947), pp. 925–929.
Franke et al., Ind. and Eng. Chem., vol. 44, No. 11 (1952), pp. 2784–2785.
Benning, Ch. Abst., vol. 49 (1955), 14293d.
Meiji Daigaku Nogakubu Kenkyu Hokoku, vol. 14, 1962, pp. 27–35, vol. 15, 1962, pp. 47–60.
Fieser et al., Advanced Organic Chem. (1961), pp. 388–391.
Wagner et al., Soil Science Soc. Am. Proc. 29(1), pp. 43–48 (1965), Chem. Abstracts, vol. 63, 1965, col. 10609.
Fuchs et al., Industrial and Engineering Chem., 35(3), 1943, pp. 343–345.
Wood et al., Fuel, 40 (1961), pp. 491–502.

Primary Examiner—Natalie Trousof
Assistant Examiner—Bernard Dentz

[57] ABSTRACT

A mixture of polycyclic aromatic polycarboxylic anhydrides carrying nuclear nitro groups that is substantially soluble in acetone but substantially insoluble in water and a process for preparing the mixture.

9 Claims, No Drawings

AROMATIC ANHYDRIDES

BACKGROUND OF THE INVENTION

1. Field of the Invention

This invention relates to a mixture of polycyclic aromatic polycarboxylic anhydrides carrying nuclear nitro groups that is substantially soluble in acetone but substantially insoluble in water and a process for preparing the mixture by treating a carbonaceous material with nitric acid and dehydrating the resulting product.

2. Description of the Prior Art

Aromatic anhydrides, such as benzophenone-3,4,3',4'-tetracarboxylic dianhydride and pyromellitic anhydride, are useful compounds as curing agents, for example, in combination with epoxy resins. These materials, however, are costly and it would be desirable to prepare aromatic anhydrides that would similarly be useful as curing agents but that would be inexpensive.

SUMMARY OF THE INVENTION

I have found a curing agent that is both effective and inexpensive to produce, which curing agent is composed of a mixture of polycyclic aromatic polycarboxylic anhydrides carrying nuclear nitro groups that is substantially soluble in acetone but substantially insoluble in water obtained as a result of the nitric acid oxidation of a carbonaceous material, such as coal, followed by dehydration. The precursor polycyclic aromatic polycarboxylic acid mixture can be prepared in accordance with the procedure defined and claimed in U.S. application Ser. No. 696,752, filed concurrently herewith by J. G. D. Schulz and E. T. Sabourin entitled Organic Acids and Process for Preparing Same and now U.S. Pat. No. 4,052,448.

The individual components of the mixture of polycyclic aromatic polycarboxylic anhydrides claimed herein are believed to be composed of condensed and/or non-condensed benzene rings, with an average number of benzene rings in the individual molecules ranging from two to about ten, but generally from three to about eight. On the average, the number of carboxyl groups carried by the individual molecules will range from about zero to about eight, generally from about zero to about six, the average number of anhydride groups carried by the individual molecules will range from about one to about five, generally from about one to about four, and the average number of nitro groups from about one to about four, generally from about two to about three. The average molecular weight of the mixture will range from about 600 to about 1500, generally from about 700 to about 1000, and the average neutral equivalent will range from about 80 to about 200, generally from about 100 to about 150.

A preferred procedure for obtaining the above mixtures is described as follows. There is introduced into a reactor an aqueous solution of nitric acid and a carbonaceous material. The nitric acid can have a concentration of about five to about 90 percent, but preferably will be in the range of about 10 to about 70 percent. The carbonaceous material is preferably a solid in the form of a slurry, for example, an aqueous slurry containing the carbonaceous material in particulate form and from about 50 to about 90 weight percent of water.

The solid carbonaceous material that can be used herein can have the following composition on a moisture-free basis:

TABLE I

| | Weight Per Cent | |
|---|---|---|
| | Broad Range | Preferred Range |
| Carbon | 45–95 | 60–92 |
| Hydrogen | 2.5–7 | 4–6 |
| Oxygen | 2.0–45 | 3–25 |
| Nitrogen | 0.75–2.5 | 0.75–2.5 |
| Sulfur | 0.3–10 | 0.5–6 |

The carbon and hydrogen content of the carbonaceous material will reside primarily in multi-ring aromatic compounds (condensed and/or uncondensed), heterocyclic compounds, etc. Oxygen and nitrogen are believed to be present primarily in chemical combination. Some of the sulfur is believed to be present in chemical combination with the aromatic compounds and some in chemical combination with inorganic elements associated therewith, for example, iron and calcium.

In addition to the above the solid carbonaceous material being treated herein will also contain solid, primarily inorganic, compounds which will not be converted to the desired organic mixture, which are termed ash, and are composed chiefly of compounds of silicon, aluminum, iron and calcium, with smaller amounts of compounds of magnesium, titanium, sodium and potassium. The ash content of the carbonaceous material treated will amount to less than about 50 weight percent, based on the moisture-free carbonaceous material, but, in general, will amount to about 0.1 to about 30 weight percent, usually about 0.5 to about 20 weight percent.

Anthracitic, bituminous and subbituminous coal, lignitic materials, and other type of coal products referred to in ASTM D-388 are exemplary of the solid carbonaceous materials which can be treated to produce the organic mixture. Some of these carbonaceous material in their raw state will contain relatively large amounts of water. These can be dried prior to use herein. The carbonaceous material, prior to use, is preferably ground in a suitable attrition machine, such as a hammermill, to a size such that at least about 50 percent of the carbonaceous material will pass through a 40-mesh (U.S. Series) sieve. As noted, the carbonaceous material is slurried in a suitable carrier, preferably water, prior to reaction with nitric acid. If desired, the carbonaceous material can be treated, prior to reaction herein, using any conventional means, to remove therefrom any materials forming a part thereof that will not be converted in reaction with nitric acid herein.

The reactant mixture in the reactor is stirred while being maintained at a temperature of about 15° to about 200° C., preferably about 50° to about 100° C., and a pressure of about atmospheric to about 1000 pounds per square inch gauge (about atmospheric to about 70 kilograms per square centimeter), preferably about atmospheric to about 500 pounds per square inch gauge (about atmospheric to about 35 kilograms per square centimeter) for about 0.5 to about 15 hours, preferably about two to about six hours. In order to obtain the desired mixture without losing appreciable amounts of carboxyl and/or nitro groups on the acids that are formed during the oxidation, and to obtain the desired acids in high yields in the reactor, it is absolutely critical that the reaction conditions therein, namely nitric acid concentration, temperature, pressure and reaction time, be so correlated to minimize and, preferably, to avoid decarboxylation and denitrofication. Gaseous products, such as nitrogen oxides, can be removed from reactor by any suitable means.

The reaction product removed from the reactor is found to be soluble, or reactable with, sodium hydroxide. At this point it is necessary to separate the oxidized product from the water and nitric acid associated therewith. This separation must be accomplished in a manner so that the carboxyl and nitro groups are not removed from the acid product. Distillation for the removal of water will not suffice, because under the conditions required for such separation, a significant loss of carboxyl groups and nitro groups would occur. A mechanical separation will, however, suffice. The reaction product is therefore led to a first separator, which can be, for example, a filter or a centrifuge.

The solids that are recovered in the separator, also soluble in sodium hydroxide, are led to a second separator wherein they are subjected to extraction with acetone. Such separation can be carried out at a temperature of about 20° to about 60° C., preferably about 25° to about 50° C., and a pressure of about atmospheric to about 500 pounds per square inch gauge (about atmospheric to about 35 kilograms per square centimeter), preferably about atmospheric to about 100 pounds per square inch gauge (about atmospheric to about seven kilograms per square centimeter). The solid material, insoluble in acetone, is removed from the latter separator by a first line and the acetone solution of the acid mixture by a second line. The acetone solution is then led to drier wherein acetone is separated therefrom and an acetone-soluble, water-insoluble polyaromatic, polycarboxylic acid mixture is recovered. As before, the acid mixture in the drier must be treated by so correlating the conditions therein to remove acetone therefrom in such manner so as to minimize and, preferably, avoid, decarboxylation and denitrofication. The temperature can be in the range of about 10° to about 60° C., preferably about 20° to about 50° C., the pressure about 10 millimeters of mercury to about atmospheric, preferably about 30 millimeters of mercury to about atmospheric, for about 0.5 to about 25 hours, preferably about one to about five hours.

Although it has been stated above that the acid mixture is acetone-soluble and acetone has been shown as suitable in the process, this has been done merely as a characterization of the composition and to exemplify one embodiment of the process. Many polar solvents can be used in place of acetone. Among the polar solvents that have been used are methanol, ethanol, isopropanol, methyl ethyl ketone, tetrahydrofuran, dioxane, etc. The use of such solvents, therefore, fall within the scope of the invention claimed herein.

The filtrate obtained in the first separator will contain water, nitric acid and most of the inorganic material (ash) that was present in the carbonaceous charge. In addition there can also be present other oxidized material, which are primarily acetone-soluble, water-soluble organic acids.

In the final stage the acetone-soluble, water-insoluble polyaromatic, polycarboxylic acid mixture is then subjected to dehydration, using any known or convenient procedure, to obtain the corresponding anhydride mixture claimed herein. If desired, the dehydration can be effected using well-known chemical dehydration agents, such as acetic anhydride, anhydrous magnesium, sodium sulfate, etc. In such case the mixture of acids is mixed with from about one to about 80 weight percent, preferably about ten to about 50 weight percent, of the dehydrating agent, at a temperature on the order of about 50° to about 250° C., preferably about 100° to about 200° C., for a time sufficient to remove chemically water from the acid mixture, for example a period of about 0.5 to about 10 hours, preferably about one to about five hours. Dehydration of the acid mixture to obtain the desired corresponding anhydride mixture can also be effected by heating the mixture without a dehydrating agent at a temperature of about 50° to about 250° C., preferably about 100° to about 200° C. and atmospheric pressure for about 0.5 to about 10 hours, preferably about one to about five hours. This heating is preferably carried out using a carrier, such as p-xylene, dixylylethane, toluene, mineral oil, or other inert solvents which will preferably form a low-boiling azeotrope with water, easily removed from the reaction zone during heating.

DESCRIPTION OF PREFERRED EMBODIMENTS

Several runs were carried out in which a North Dakota lignite analyzing as follows, on a substantially moisture-free basis, was subjected to oxidation using nitric acid as the oxidant: 65.03 weight percent carbon, 4.0 weight percent hydrogen, 27.0 weight percent oxygen, 0.92 weight percent sulfur, 0.42 weight percent nitrogen and 0.04 weight percent moisture. The ash was further analyzed and found to contain 43 weight percent oxygen, 7.8 weight percent sulfur and the remainder metals.

In each of Runs Nos. 1 to 3, the data of which are summarized below in Table III, 70 percent aqueous nitric acid was used. In Runs Nos. 2 and 3 over a period of two hours 100 milliliters of the defined nitric acid was gradually added to the stirred slurry containing 100 grams of powdered lignite defined above (corresponding to 67.5 grams of moisture-free feed) and 370 grams of water while maintaining the contents at selected temperature levels and atmospheric pressure. In Run No. 1, otherwise identical to Runs Nos. 2 and 3, a five-hour reaction time was employed. Nitrogen oxides were permitted to escape from the reaction zone as they evolved.

At the end of the reaction period the product slurry was withdrawn from the reaction zone and filtered to obtain a solids fraction and a filtrate. The solids were extracted with acetone at atmospheric temperature and pressure. The acetone solution was then subjected to evaporation at atmospheric temperature and pressure to obtain the acid mixture. The acetone insoluble portion was found to be soluble in sodium hydroxide and to comprise organic acids of a relatively lower carboxyl functionality than the acetone-soluble portion.

In each of the runs some acetone soluble, water-soluble organic acids were also found. The work-up of the filtrate was carried out as follows. Initially the filtrate was subjected to distillation to separate unreacted nitric acid and water therefrom. The remaining solids were subjected to extraction with acetone at atmospheric temperature and atmospheric pressure. The acetone solution was dried to remove acetone therefrom, resulting in the recovery of small amounts of the acetone-soluble, water-soluble organic acids completely soluble in sodium hydroxide. The average molecular weight of the mixtures obtained was about 800 and the average neutral equivalent about 110. The residue was mainly ash.

In separate runs, 30 grams of the acetone-soluble mixture recovered above was mixed with 150 grams of mixed xylenes and the resulting mixture was heated to reflux temperature and maintained at such temperatures, while stirring, for two hours. In each instance about 2.2 grams of water was evolved, indicating dehydration of the acid mixture. The presence of anhydride in the infra-red spectrum of each product obtained further proved dehydration had taken place. In each instance the neutral equivalent was found to be 119.

In a separate run, 50 grams of another portion of the acetone-soluble mixture obtained in Run No. 3 was mixed with 150 grams of acetic anhydride and 200 grams of tetrahydrofuran as a solvent. The mixture was brought to reflux temperature and maintained at such temperature, while stirring, for 16 hours. The product, 24 grams which was found to be totally soluble in the tetrahydrofuran-acetic anhydride mixture, was recovered by evaporation of the solvent at 35° C. The neutral equivalent was found to be 105. The presence of anhydride bands in the infra-red spectrum of the product is indicative of dehydration. The results obtained are tabulated below in Table II.

1200 pounds per square inch gauge (70.5 to 84.4 kilograms per square centimeter) over a period of one-half hour. A good black disc was again prepared. The product was post cured at 175° C. for 16 hours to obtain a final product having a Barcol hardness of 25 to 28.

Obviously, many modifications and variations of the invention, as hereinabove set forth, can be made without departing from the spirit and scope thereof and, therefore, only such limitations should be imposed as are indicated in the appended claims.

I claim:

1. A mixture of polycyclic aromatic polycarboxylic anhydrides carrying nuclear nitro groups obtained by a process which consists essentially in subjecting a slurry containing coal in particulate form and from about 50 to about 90 weight percent water to reaction with aqueous nitric acid having a concentration of about five to about 90 percent at a temperature of about 15° to about 200° C. for about 0.5 to about 15 hours, mechanically separating the solids in the resulting slurry, extracting the resulting solids with a polar solvent, separating the polar solvent from the extract to recover the carboxylic acid mixture and then subjecting said acid mixture to

TABLE II

| Run No. | Temperature, °C. | Reaction Time, Hours | Acetone-Soluble Water-Insoluble Product, Grams | Analysis of Acid Product, Weight Percent | | | | | | Neutral Equivalent of Anhydride Mixture |
|---|---|---|---|---|---|---|---|---|---|---|
| | | | | Carbon | Hydrogen | Nitrogen | Oxygen | Sulfur | Ash | |
| 1 | 50 | 5 | 67.0 | 56.30 | 4.80 | 4.60 | 33.27 | 0.31 | 0.72 | 119 |
| 2 | 70 | 2 | 51.1 | 55.52 | 3.72 | 4.70 | 35.13 | 0.30 | 0.63 | 119 |
| 3 | 90 | 2 | 52.5 | 53.94 | 4.38 | 4.61 | 36.39 | 0.25 | 0.43 | 119,105 |

The anhydride mixtures obtained herein are effective curing agents. This is shown below.

EXAMPLE I

Twenty-five grams of EPON 1004 (Shell Chemical Company), an epoxy resin believed to be the diglycidyl ether of Bisphenol A having an epoxy equivalent of 900, 10.5 grams of the anhydride mixture from Run No. 3, above, prepared using acetic anhydride as a dehydrating agent, and 0.9 gram of tin octanoate as an accellerator intimately mixed, the mixture was added to a ceramic jar and rolled with burundum cylinders for 24 hours. Circular molded discs were prepared at 165° C., 1600 pounds per square inch gauge 112.5 kilograms per square centimeter) and two hour molding time. The initial Barcol hardness was from 6 to 8. When the discs were post cured overnight at 175° C., the hardness increased to 12 to 16.

EXAMPLE II

Nine grams of EPON 1004, 20 grams of the same anhydride mixture used in Example I and 0.9 gram of tin octanoate were ball milled overnight to obtain a powdered mixture. Molded products were prepared by molding the product at 175° C. and a pressure of 1000 to dehydration to obtain the corresponding anhydride mixture.

2. The composition of claim 1 wherein the polar solvent is acetone.

3. The composition of claim 1 wherein the nitric acid has a concentration of about 10 to about 70 percent and the reaction is carried out at a temperature of about 50° to about 100° C. for about two to about six hours.

4. The composition of claim 1 wherein the mechanical separation is effected by filtration.

5. The composition of claim 1 wherein the polar solvent separation is effected by subjecting the polar solvent extract to evaporation.

6. The composition of claim 1 wherein said dehydration is effected by treatment with a chemical dehydrating agent.

7. The composition of claim 6 wherein said dehydrating agent is acetic anhydride.

8. The composition of claim 1 wherein said dehydration is effected by heating the acid mixture at a temperature of about 50° to about 250° C.

9. The composition of claim 1 wherein said dehydration is effected by heating the acid mixture at a temperature of about 100° to about 200° C.

* * * * *